United States Patent [19]
Cardinal et al.

[11] Patent Number: 5,122,128
[45] Date of Patent: Jun. 16, 1992

[54] ORIFICE INSERT FOR A RUMINAL BOLUS

[75] Inventors: John R. Cardinal, North Wales, Pa.; Paul K. Wilkinson, Ann Arbor, Mich.; Joel R. Zingerman, Westfield, N.J.

[73] Assignee: ALZA Corporation, Palo Alto, Calif.

[21] Appl. No.: 493,596

[22] Filed: Mar. 15, 1990

[51] Int. Cl.$^5$ ............................................. A61K 9/22
[52] U.S. Cl. ................................................ 604/890.1
[58] Field of Search ............. 604/890.1, 891.1, 892.1, 604/57; 424/422, 438, 464, 468

[56] References Cited

U.S. PATENT DOCUMENTS

| | | | |
|---|---|---|---|
| 3,760,804 | 9/1973 | Higuchi et al. | 604/892.1 |
| 3,995,632 | 12/1976 | Nakano et al. | 604/892.1 |
| 4,312,347 | 1/1982 | Magoon et al. | 604/891.1 |
| 4,416,659 | 11/1983 | Simpson | 604/57 |
| 4,425,117 | 1/1984 | Hugemann et al. | 604/890.1 |
| 4,772,474 | 9/1988 | Eckenhoff et al. | 604/892.1 |
| 4,872,873 | 10/1989 | Zingerman | 604/892.1 |

FOREIGN PATENT DOCUMENTS 0321043  6/1989  European Pat. Off. .

Primary Examiner—C. Fred Rosenbaum
Assistant Examiner—Sharon Finkel
Attorney, Agent, or Firm—Jacqueline S. Larson; Edward L. Mandell; Steven F. Stone

[57] ABSTRACT

There is disclosed an insert for the orifice of a ruminal bolus. The insert fits within the exit orifice of the ruminal bolus such that the medicated paste being discharged passes through the insert creating a back pressure within the paste compartment of the bolus which improves the performance of the bolus. The insert also prevents foreign objects from becoming lodged in the orifice. The insert consists of a grid-like series of openings with insert members extending into the orifice for a significant portion of the total length. Integral with the insert is a flange which secures the insert within the orifice and prevents it from being removed from the orifice or from being driven into the orifice.

11 Claims, 5 Drawing Sheets

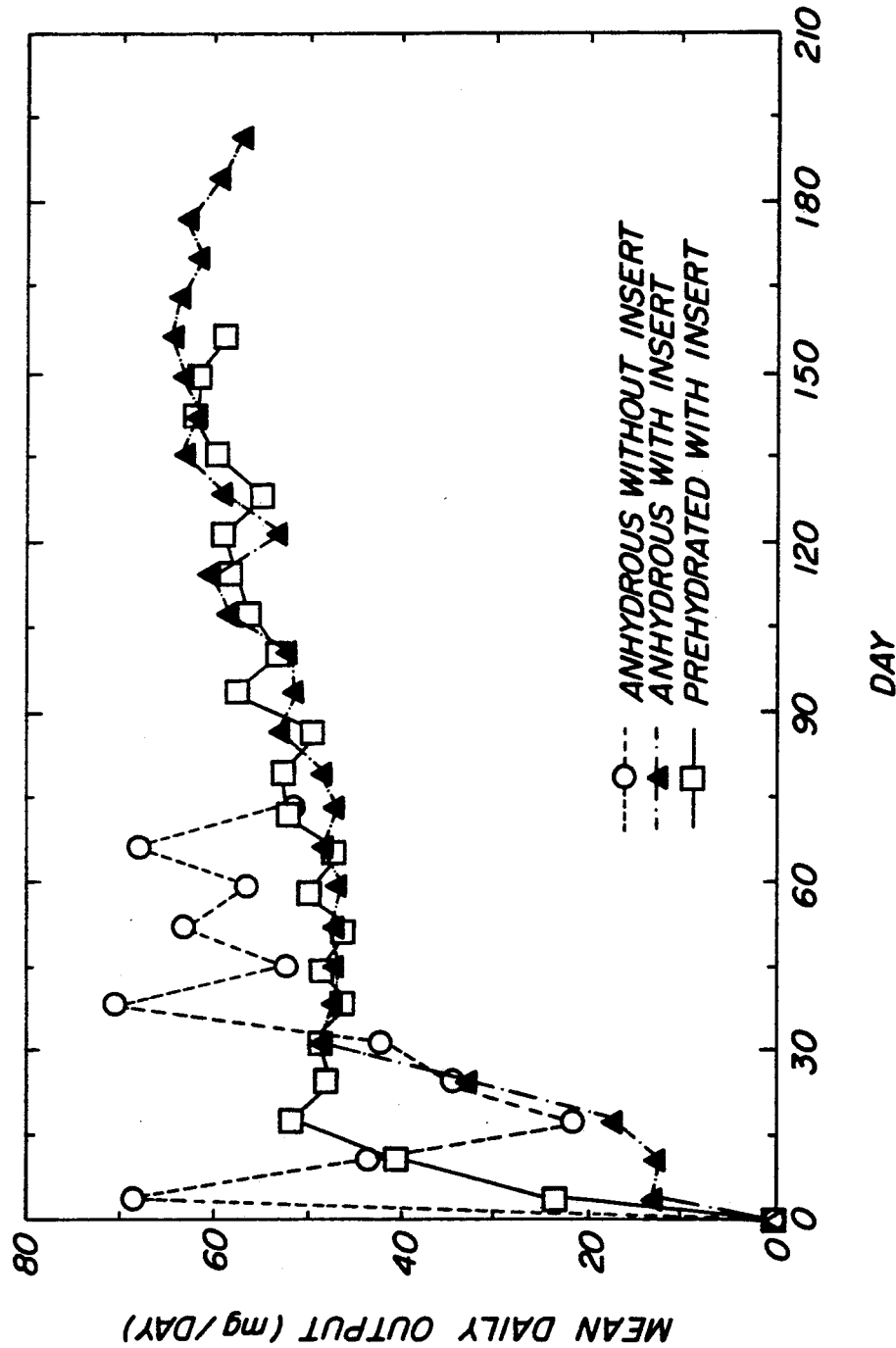

ORIFICE INSERT FOR A RUMINAL BOLUS

BACKGROUND OF THE INVENTION

Throughout the art is disclosed numerous controlled release devices for administering medication such as drugs, as well as food supplements such as vitamins to animals such as livestock, (e.g., horses, cattle, pigs, etc.). Heretofore, said medication was primarily administered to animals via feed and syringe methods.

Representative controlled delivery devices disclosed in the art are indicated below:

1.) U.S. Pat. No. 4,200,098 (1980)—osmotic system is disclosed for dispensing a beneficial agent. The system comprises (1) a first wall of a semipermeable material that surrounds a compartment containing a drug formulation, and has a passageway through the wall for releasing agent from the compartment, (2) a second wall positioned distant from the first wall, said second wall a microporous or hydrogel material that extends around the first wall, and (3) a distribution zone interposed between the first and second wall and initially housing a compound soluble in an external fluid that enters the system.

2.) U.S. Pat. No. 4,077,407 (1978)—discloses an osmotic device for delivering an active agent. The device is comprised of a wall surrounding a compartment and has a passageway through the wall for releasing the agent. The wall is formed of a multiplicity of materials comprising a material permeable to an external fluid and substantially impermeable to agent and at least one additional material selected from a material that imparts stability to the wall, enhances the permeability of the wall to fluids, or aids in forming the wall. The compartment comprises an active agent that exhibits an osmotic pressure gradient against an external fluid, or the agent is mixed with an osmotically effective compound that exhibits an osmotic pressure gradient against the fluid. Agent is released from the device by fluid being imbibed through the wall into the compartment at a rate controlled by the permeability of the wall and the osmotic pressure gradient across the wall, to produce a solution containing agent that is released through the passageway at a controlled and continuous rate over a prolonged period of time.

3.) U.S. Pat. No. 4,160,020 (1979)—An osmotic device is disclosed for delivering an active agent. The device comprises a wall surrounding a compartment with a passageway through the wall for releasing the agent. The wall comprises a material permeable to an external fluid and substantially impermeable to agent and at least one additional material independently selected from materials that impart stability to the wall, enhance the permeability of the wall to fluids, or aid in forming the wall. The compartment contains an agent that exhibits an osmotic pressure gradient across the wall against an external fluid, or the agent is mixed with an osmotically effective compound that exhibits an osmotic pressure gradient against the fluid. Agent is released from the device by fluid being imbibed through the wall into the compartment at a rate controlled by the permeability of the wall and the osmotic pressure gradient across the wall, thereby producing a solution containing agent that is released through the passageway at a controlled rate over time.

4.) U.S. Pat. No. 4,327,725 (1982)—An osmotic device is disclosed comprising a semipermeable wall surrounding a compartment housing an agent that is insoluble to very soluble in aqueous and biological fluids, and a layer of a fluid swellable, hydrogel. A passageway in the wall connects the agent with the exterior of the device.

SUMMARY OF THE INVENTION

The instant invention is concerned with a device which improves the performance of a ruminal bolus, in particular a ruminal bolus designed for extended duration therapy, as long as 60 to 120 days. The improvement consists of an insert which fits over and within the exit orifice for the medicated paste being expelled from the bolus. Thus, it is an object of this invention to describe such a device. A further object is to describe the improved performance of the ruminal bolus which results when the insert is placed within the orifice. Further objects will become apparent from a reading of the following description.

DESCRIPTION OF THE INVENTION

A ruminal bolus is a device which provides a source of medically or nutritionally useful material for a prolonged period of time. Traditionally boluses have been large tablets which provide a prolonged release of the active material by a delayed erosion process, perhaps through a laminated structure. A more recent development has been the osmotically driven ruminal bolus which is placed in the rumen and retained there with a densifier which prohibits regurgitation, and which has an osmotic portion which imbibes ruminal fluid and expands, forcing a liquid or paste portion of the bolus through an orifice into the rumen. The osmotic ruminal bolus has encountered some difficulties, however. During the ingestion of hay, the ruminant may also ingest pieces of baling wire, fencing or nails which, since the bolus is retained in the rumen for a prolonged period of time, may enter the exit orifice and block the flow of the medicated portion of the bolus through the orifice. Because the osmotic portion will still imbibe fluid and expand, a blocking of the orifice could cause the bolus to rupture and release all of its contents at once, which could have very serious adverse consequences for the ruminant, especially if the rupture occurred during the early portion of the lifetime of the bolus.

Thus, the instant insert has the advantage of preventing the entry of foreign objects into the orifice. However, the insert has had the unexpected effect of actually improving the performance of the bolus. The placement of the insert appears to cause an increase in the back pressure upon the medicated paste portion of the bolus, which has been found to provide a more uniform release profile of the medicated portion of the bolus. In comparative tests of the bolus with and without the instant insert, the daily output of the bolus is seen to be highly erratic while the same device with the instant insert in place achieves a highly uniform, steady state output in a very short time. While not being bound by theory, it appears that the insert increases the back pressure on the medicated paste and prevents the accumulation of gas bubbles which can cause fissures within the medicated paste medium. The presence of such fissures can cause gaps in the flow of medicated paste or, when a fissure nears the base of the orifice, a rapid expulsion of a portion of medicated paste. Thus erratic flow is observed with days of low output and days of high output. The instant invention has eliminated this problem. In addition, the insert, with its grid-like openings forming passageways, divides the existing cylindrical column of paste into a multitude of smaller columns which, because of a significant increase in surface area, is more readily dispersed throughout the ruminal fluid thus making it more rapidly utilized by the ruminant.

As will be explained below, the various arrangements of the insert such as the number, shape and area of the passageways, the shape of the orifice, and the like can be varied to adjust the degree of increased back pressure caused by the insert, and thus control the operation of the bolus.

The insert is characterized in that it has an axially arranged insert portion and a cap or retaining portion. The insert portion has the same outside cross-sectional shape as the inside cross-sectional shape of the bolus orifice. Generally this cross sectional shape is circular; however, other cross sectional shapes are also possible. The outside diameter of the insert portion is substantially the same size as the orifice to ensure a tight fit to assist in preventing the dislodgement of the insert.

The upper end of the insert is of an expanded shape to form a cap portion which conforms to the outside shape of the bolus in the area immediately surrounding the orifice. In addition, through attachment means such as by crimping a portion of the bolus material over the outside edge of the cap portion, the entire insert is permanently retained within and surrounds the bolus orifice. The cap portion, being larger than and integral with the insert portion, will prevent the insert from being driven into the orifice, and the friction of the insert portion against the orifice along with the attachment means of the cap portion, will prevent the insert from being forced out of the orifice by the pressure of the osmotically driven paste.

The insert is provided with a grid-like cross section with a rectangular array of cross members which provides for a multitude of openings or passageways within the insert which break up the stream of paste exiting the bolus into many smaller streams.

The shape of the individual openings can be of any convenient shape such as square, circular, rectangular, polygonal, etc. For ease of manufacturing a square or circular shape is generally preferred. The insert portion of the insert generally extends into the orifice a distance which is sufficient to provide adequate friction to prevent the dislodgement of the insert. This distance is generally at least 10% up to 100% of the length of the orifice. Preferably the insert portion is from about 10% to 25% of the length of the orifice. Most preferably the orifice is about 12% of the length of the orifice.

An optional arrangement for the insert portion is to provide for an expanded portion of the orifice at the exterior end of the orifice in which the insert portion resides. At the point where the orifice narrows, a ledge will be formed which will be at a distance from the end of the orifice which corresponds to the length of the insert portion. By having a ledge against which the lower edge of the perimeter of the insert portion rests, the insert will be completely prevented from being driven into the bolus by the force of an object pushing against the insert. In addition, the outer circumferential edge of the insert portion would not block the flow of the exiting paste and the paste would only have to flow past the inner cross members of the insert. Thus, the use of an expanded portion of the orifice can be used to regulate the degree of back pressure against the paste.

The degree of back pressure can also be regulated by the size and arrangement of the cross members within the insert portion. The ratio of the area of the passageways to the area of the cross members is preferably about 1:1. That is, the cross members reduce the total cross sectional area of the orifice by about 50%. Other arrangements with narrower or wider cross members relative to the total area of the passageways can provide for ratios of from about 1:2 to 2:1. In such cases the cross sectional area of the orifice is reduced by about ⅓ to about ⅔ respectively. Higher levels of cross sectional area of the cross members will cause a higher back pressure while lower levels of cross sectional area of the cross members will cause a lower back pressure.

In addition, the lower edges of the cross members, the edges facing into the bolus, can be shaped to have an effect upon the back pressure. "Squared-off" lower edges, with a surface perpendicular to the flow of the paste will tend to provide a greater resistance to the flow of the paste and thus increase the back pressure. Optionally the surface can be beveled to provide a pointed surface or the surface can be approximately semicircular to provide for a rounded surface, which will tend to minimize the effect of the shape of the lower edge upon the flow of paste, and consequently the back pressure.

The improved controlled release bolus of this invention comprises a semipermeable membrane which defines a compartment, the compartment being divided into first and second portions by a moveable interface. The first compartment portion contains a swellable osmotic material and the second compartment portion contains a medicament to be dispensed, generally in a semiliquid or paste form. A densifier resides within the second compartment adjacent said membrane. An orifice having an inside cross sectional shape and extending through the membrane and densifier connects said second compartment portion with the exterior of the bolus. When the bolus is in contact with water such as is found in the ruminal fluid of a ruminant, the semipermeable membrane allows water to pass therethrough which is imbibed by the swellable osmotic agent which forces the interface to move the medicament to be dispensed through the orifice. The improvement of this invention comprises an insert which is placed coaxially within the orifice at the point nearest the exterior of the bolus, said insert comprising an insert portion of the same outside cross-section shape as the inside cross section shape of the orifice and having a grid-like structure extending the length of the insert providing multiple passageways through the insert and the insert portion, and a cap portion integral with the insert portion and of a greater diameter than the insert portion shaped to allow for attachment means to the area of the bolus surrounding the orifice, where the orifice exits the bolus.

Additional details of the ruminal bolus insert are found in the appended drawings:

FIG. 8 is a plot of the mean daily output of the ruminal bolus with and without the insert, verses time.

Figure 1:
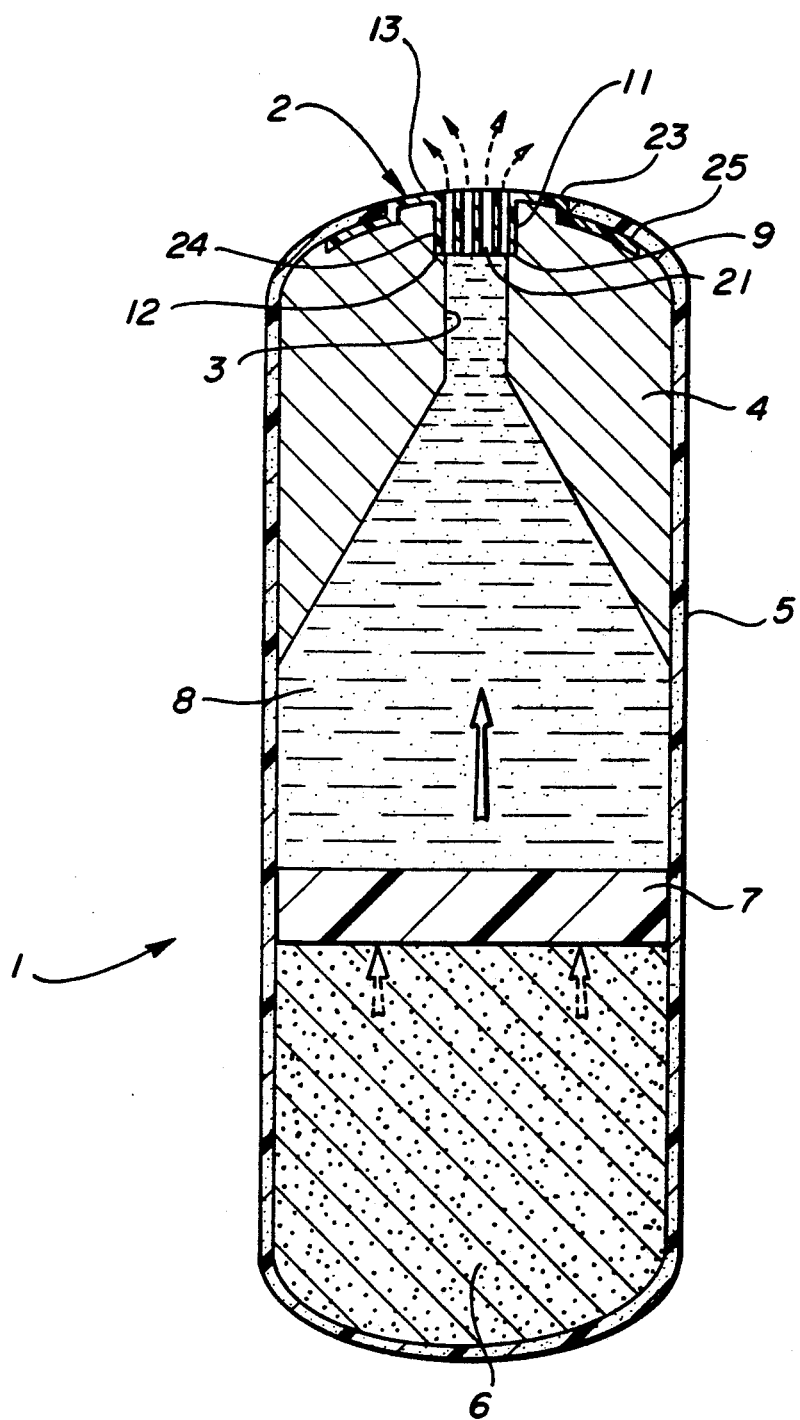
FIG. 1 is a cross-section of the entire ruminal bolus showing the insert installed in the orifice.

In FIG. 1, 1 is the osmotically driven ruminal bolus with the insert 2 showing the passageways 21. The insert resides in the orifice 3 which passes through the densifier 4. The bolus is surrounded by a semipermeable membrane 5. The semipermeable membrane 5 allows water to pass therethrough which is imbibed by the swellable osmotic element 6 which, upon imbibing the water exerts force upon the moveable interface 7 which in turn forces the medicament 8 out of the orifice 3 and through the passageways 21 of the insert 2.

Additionally, FIG. 1 shows the arrangement of the insert where the insert portion 24 resides in an expanded portion of the orifice 3 such that a ledge 9 is formed at the point where the expanded portion 11 and narrowed portion 10 of the orifice 3 meet. The lower circumferential edge 12 of the insert portion 24 rests upon the ledge 9 and prevents further entry of the insert into the orifice.

FIG. 1 also shows the cap portion 13 of the insert with the provision for anchoring or securing the cap portion 13 to the bolus 1 wherein the cap portion 13 contains an inner portion 23 and an outer portion 25 such that the semipermeable membrane 5 can be made to overlay the outer portion 25 to prevent the ejection of the insert 2. The cap portion 13 can also be secured to the bolus 1 by cementing or other securing means.

Figure 2A:
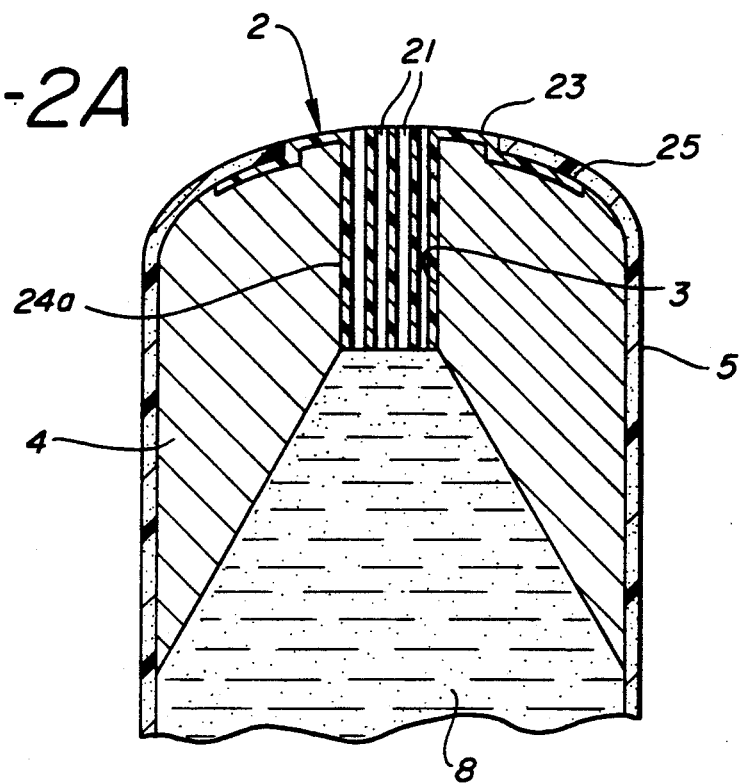
FIGS. 2A and 2B are enlarged cross-sections of the ruminal bolus showing alternate arrangements of the insert within the orifice.

FIG. 2A shows an alternate arrangement wherein an elongated insert portion 24a is provided extending substantially the entire length of the orifice 3.

Figure 2B:
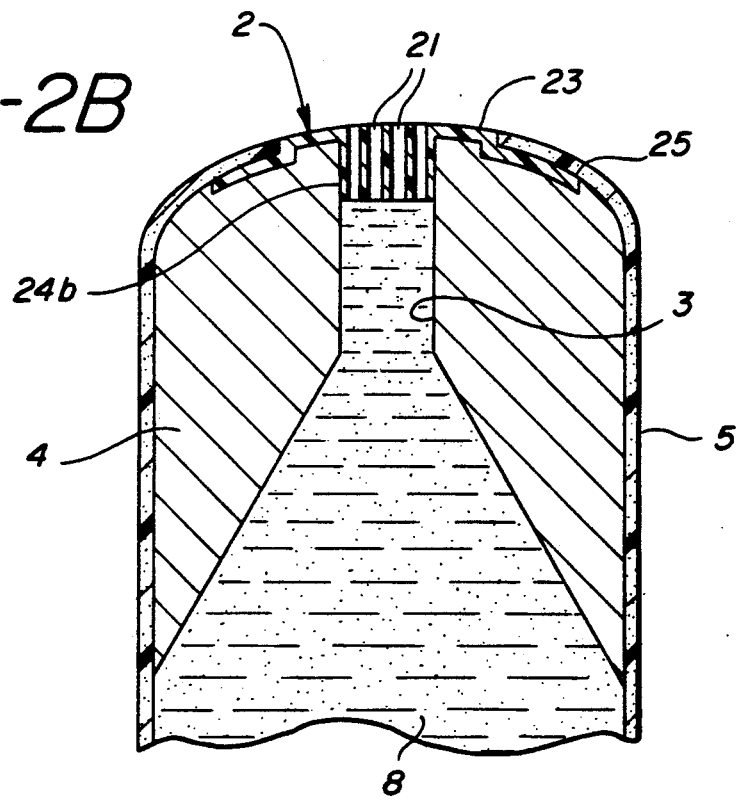

FIG. 2B shows a further alternate arrangement of the insert 2 in the orifice 3 where a shortened insert portion 24b resides in the orifice 3 and wherein the outside shape and size of the insert portion 24b is substantially the same as the inside shape and size of the orifice 3.

Figure 3:
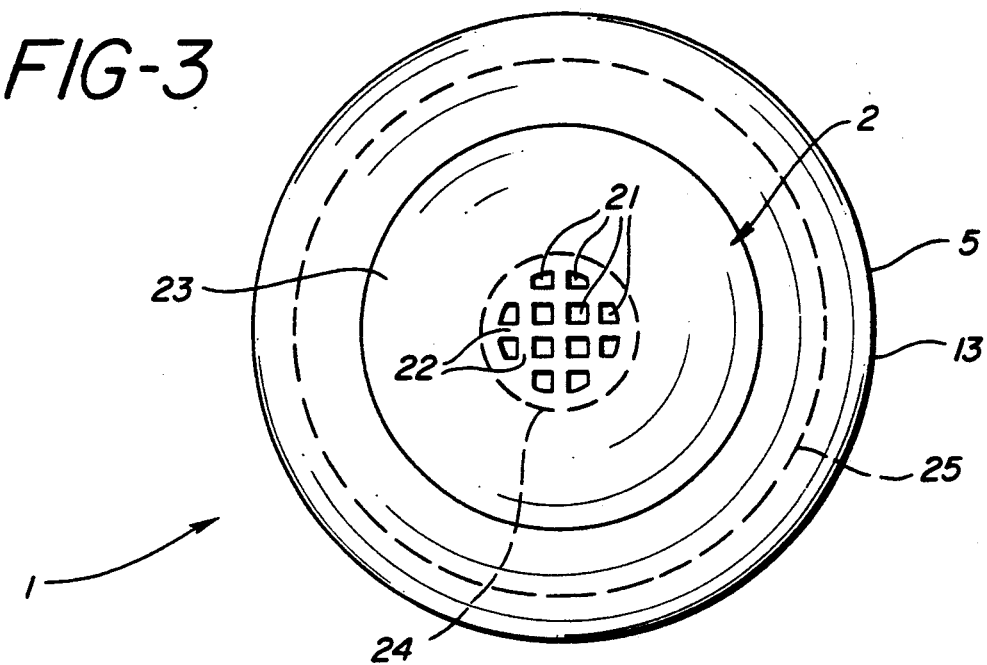
FIG. 3 is an end view of the ruminal bolus showing the insert installed in the bolus.

In FIG. 3 the grid-like structure 22 defines the passageways 21 through which the medicament passes. The cap portion 13, is larger than the insert portion 24. The insert 2 is secured to the bolus 1 by attachment means, in this case by crimping the lower cap portion 25, under the semipermeable membrane 5.

Figure 4:
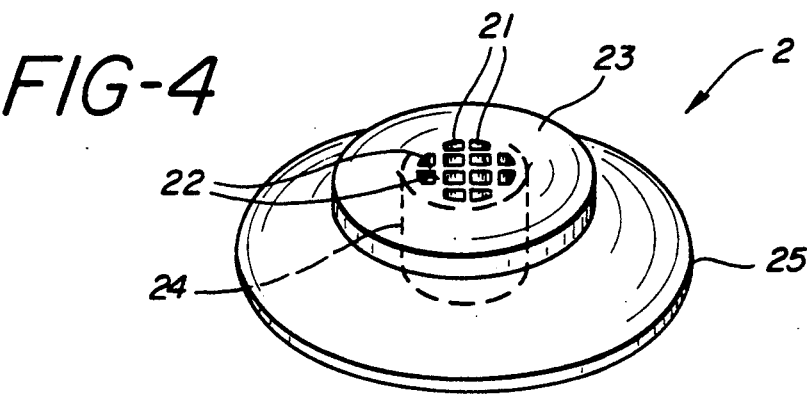
FIG. 4 is an enlarged perspective view of the insert.

In FIG. 4 the insert 2 is shown in perspective to clearly show the passageways 21 formed by the grid structure 22, and also the upper cap portion 23 and the lower cap portion 25 as means to secure the insert 2 to the bolus 1.

Figure 5:
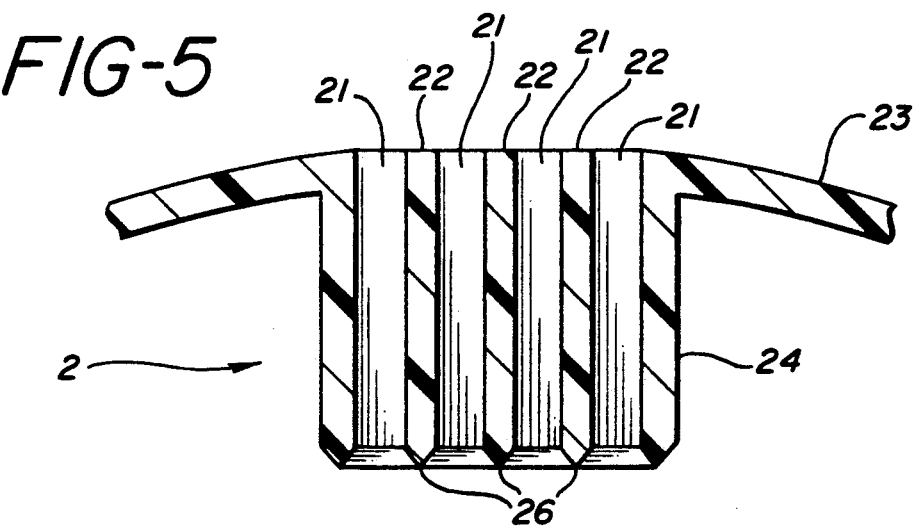
FIG. 5 is a further enlarged cross-section of the insert showing one configuration of the lower edge of the cross members.

FIG. 5 shows a further enlarged cross-section view of the insert 2 showing four passageways 21 formed by grid structure 22. In one arrangement of the lower edges 24 of the grid members 22, the lower edges 26 are arranged as bevels facing into the outflowing stream of medicated paste.

Figure 6A:
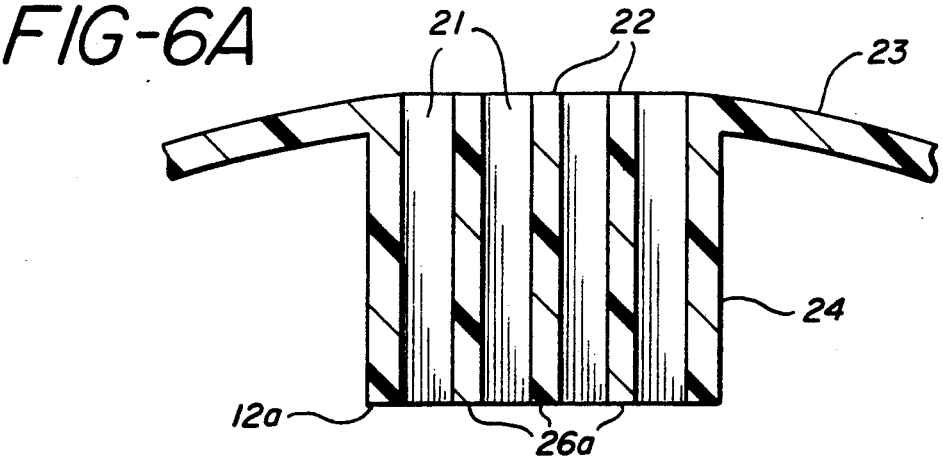
FIGS. 6A, 6B and 6C are enlarged cross-sections of the insert showing alternate arrangements of the lower edge of the cross members.
Figure 6B:
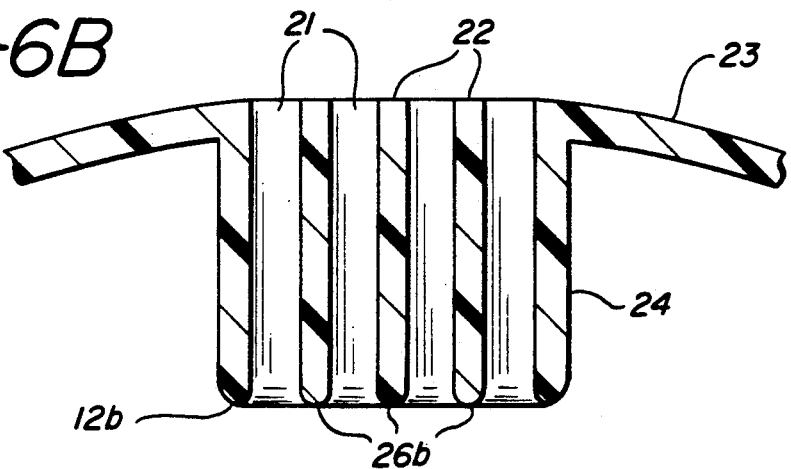
Figure 6C:
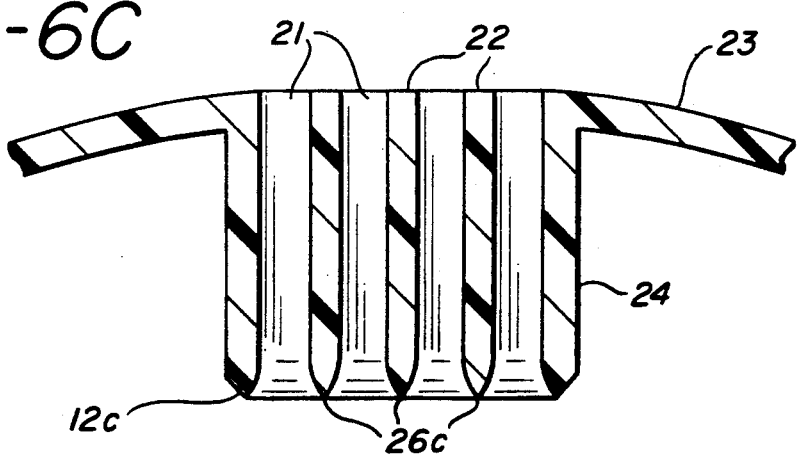

In FIG. 6A the grid members 22 are formed with square faces 26a perpendicular to the direction of the outflowing paste. FIG. 6B shows a rounded shape 26b and FIG. 6C shows a rounded beveled shape 26c. These various shapes have an effect upon the flow of paste through the insert 2 and thus affect the back pressure and thus the operation of the bolus.

The lower circumferential edges of the insert portion 24 may be squared as in 12a or, in order to facilitate the assembly of the insert into the orifice, the lower outside corners may be rounded 12b or beveled 12c.

Figure 7A:
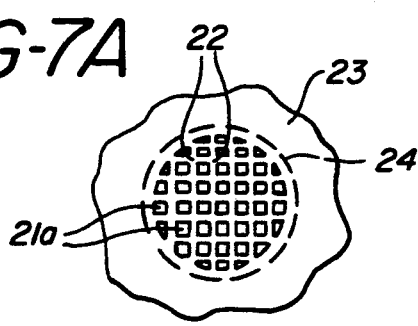
FIG. 7 is an end view of the insert showing an alternate arrangement of the passageways in the grid-like structure.
Figure 7B:
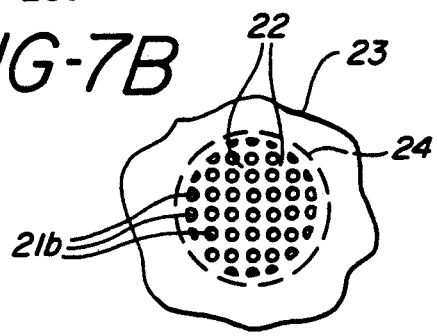

FIGS. 7A and 7B show further arrangements of the grid members 22 such that a large number of grid members are present creating a large number of passageways 21a and 21b. In FIG. 7B the passageways 21b are given a rounded shape. The various shapes of the passageways 21, 21a and 21b formed by grid members 22 provide for increased or decreased ratios of the areas of the passageways 21, 21a and 21b to the areas of the grid members 22 which affect the degree of back pressure created by the presence of the insert.

FIG. 8 shows the effect of the instant insert device on the rate of flow of the medicated paste out of the orifice. The rate of flow of the medicated paste in the bolus without the insert device is seen to be very variable, sometimes providing 20 mg per day and sometimes providing 70 mg per day. When the insert device is installed, the output is maintained at a relatively constant rate of from 50 to 60 mg per day after a brief start-up period. (The test also measured the effects of prehydrating the osmotic capsule prior to use which significantly shortened the start-up period of the bolus and which does not form part of this invention). These tests were carried out in vivo in ruminants (cattle) in which the amount of paste expelled by the bolus was measured periodically during the duration of the test.

The insert can be made out of any material which is inert to the paste material which passes therethrough and which has sufficient strength to resist deformation under the pressure exerted by the osmotic capsule upon the paste material. In addition, the material should not absorb significant amounts of water or suffer other effects, such as rusting, which would change the size of the passageways. For ease of manufacturing, materials which are readily extrudable are preferred and nylon is the most preferred material.

What is claimed is:

1. An improved controlled release bolus comprising a semipermeable membrane defining a compartment, the compartment being divided into first and second portions by a moveable interface, the first compartment portion containing a swellable osmotic agent, the second compartment portion containing a medicament to be dispensed, a densifier within the second compartment adjacent the membrane and an orifice having an inside cross-section shape and extending through the membrane and the densifier to connect the second compartment portion with the exterior of the bolus, such that when the bolus is in contact with water, the semipermeable membrane allows water to pass therethrough, which water is imbibed by the swellable osmotic agent which forces the interface to move the medicament to be dispensed through the orifice, wherein the improvement comprises an insert which is placed coaxially within the orifice at the point nearest the exterior of the bolus, said insert comprising (1) an insert portion of the same outside cross-section shape as the inside cross-section shape of the orifice and having a grid-like structure extending the length of the insert providing multiple passageways through the insert and the insert portion, and (2) a cap portion integral with the insert portion and of a greater diameter than the insert portion and shaped to allow for attachment means to the area of the bolus surrounding the orifice where the orifice exits the bolus.

2. The bolus of claim 1 wherein the passageways are of a square or circular cross-sectional shape.

3. The bolus of claim 1 wherein the insert portion has the same diameter as the diameter of the orifice.

4. The bolus of claim 1 wherein the insert portion and the section of the orifice which contacts the insert portion have a greater diameter than the diameter of the remainder of the orifice.

5. The bolus of claim 1 wherein the insert portion extends from 10% to 100% of the length of the orifice.

6. The bolus of claim 5 wherein the insert portion extends from 10% to 25% of the length of the orifice.

7. The bolus of claim 6 wherein the insert portion extends about 12% of the length of the orifice.

8. The bolus of claim 1 wherein the lower edge of the grid-like structure has a squared-off, beveled or rounded cross-section.

9. The bolus of claim 8 wherein the lower edge of the grid-like structure has a beveled cross-section.

10. The bolus of claim 1 wherein the ratio of the cross-sectional area of the grid-like structure to the cross-sectional area of the passageways is from 2:1 to 1:2.

11. The bolus of claim 10 wherein the ratio is about 1:1.

* * * * *